United States Patent
Miranda et al.

(10) Patent No.: US 7,365,208 B2
(45) Date of Patent: Apr. 29, 2008

(54) METHOD FOR PREPARING IRBESARTAN AND INTERMEDIATES THEREOF

(75) Inventors: Edgar I. Miranda, Guaynabo, PR (US); Cornelis Vlaar, San Juan, PR (US); Jingyang Zhu, Monmouth Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/688,635

(22) Filed: Mar. 20, 2007

(65) Prior Publication Data

US 2007/0167634 A1    Jul. 19, 2007

Related U.S. Application Data

(62) Division of application No. 11/209,000, filed on Aug. 22, 2005, now Pat. No. 7,211,676.

(60) Provisional application No. 60/603,606, filed on Aug. 23, 2004.

(51) Int. Cl.
   *C07D 235/02* (2006.01)
(52) U.S. Cl. .................................. 548/300.7
(58) Field of Classification Search ...................... None
   See application file for complete search history.

(56) References Cited

U.S. PATENT DOCUMENTS

| 5,270,317 | A | | 12/1993 | Bernhart et al. |
| 5,994,348 | A | | 11/1999 | Ku et al. |
| 6,162,922 | A | * | 12/2000 | Anderson et al. ........ 548/300.7 |
| 6,342,247 | B1 | | 1/2002 | Ku et al. |
| 6,800,761 | B1 | * | 10/2004 | Franc et al. ................. 548/253 |

FOREIGN PATENT DOCUMENTS

| CA | 2154807 | 2/1996 |
| EP | 0 708 103 | 1/2001 |
| WO | WO 91/14679 | 10/1991 |
| WO | WO 99/06398 | 2/1999 |
| WO | WO 99/38847 | 8/1999 |
| WO | WO 99/67236 | 12/1999 |

OTHER PUBLICATIONS

Smith, A. A. Organic Process Research & Development 1997, 1, 165-167.*

Bernhart, C.A. et al., "A New Series of Imidazolones: Highly Specific and Potent Nonpeptide $AT_1$ Angiotensin II Receptor Antagonists", J. Med. Chem., vol. 36, No. 22, pp. 3371-3380 (1993).

Cava, M.P. et al., "Nonclassical Condensed Thiophenes. VI. Isothianaphthene 2,2-Dioxides", J. Org. Chem., vol. 40, No. 1, pp. 72-77 (1975).

Diwu, Z. et al., "A Facile Protocol for the Convenient Preparation of Amino-substituted α-Bromo- and α,α-Dibromo Arylmethylketones", Tetrahedron Letters, vol. 39, pp. 4987-4990 (1998).

Hirao, T. et al., "Reduction of Organic Halides with Diethyl Phosphonate and Triethylamine", Bull. Chem. Soc. Jpn., vol. 56, No. 6, pp. 1881-1882 (1983).

Hirao, T. et al., "Versatile Synthesis of Dialkyl Cyclopropylphosphonates *via* Reductive Phsophonation", Bull. Chem. Soc. Jpn., vol. 58, No. 11, pp. 3104-3107 (1985).

Hirao, T. et al., "Versatile Synthesis of Diethyl Cyclopropanephosphonates", Synthesis, pp. 60-61 (1984).

Liu, P. et al., "An Efficient Method for the Preparation of Benzylic Bromides", Synthesis, No. 14, pp. 2078-2080 (2001).

Ponchant, M. et al., "Radiosynthesis of [tetrazoyl-C]irbesartan, a non-peptidic angiotensin II antagonist", Eur. J. Med. Chem., vol. 32, pp. 747-752 (1997).

Shen, J.-S. et al., "An Improvement on the Synthetic Technology of Irbesartan", Chinese Journal of Medicinal Chemistry, vol. 11, No. 2, pp. 104-106 (2001) (with English abstract).

* cited by examiner

*Primary Examiner*—Rebecca Anderson
*Assistant Examiner*—Jason M Nolan
(74) *Attorney, Agent, or Firm*—Burton Rodney; Henry Gu

(57) ABSTRACT

A method for preparing irbesartan and intermediates thereof. Irbesartan has the structure of formula I,

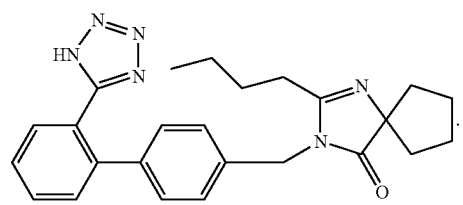

5 Claims, No Drawings

METHOD FOR PREPARING IRBESARTAN AND INTERMEDIATES THEREOF

RELATED APPLICATIONS

This application is a divisional of Ser. No. 11/209,000 filed on Aug. 22, 2005 now U.S. Pat. No. 7,211,676, which claims the priority benefit of U.S. Provisional Application No. 60/603,606 filed Aug. 23, 2004, the disclosures of which are incorporated herein by reference in their entirety.

FIELD OF THE INVENTION

The invention relates to methods for preparing irbesartan and intermediates thereof. Irbesartan is an antagonist for angiotensin II receptor and is useful for treating angiotensin II-associated disorders.

BACKGROUND OF THE INVENTION

Irbesartan is a potent, long-acting angiotensin II receptor antagonist that is especially useful in the treatment of cardiovascular ailments such as hypertension and heart failure. Irbesartan has the following structure:

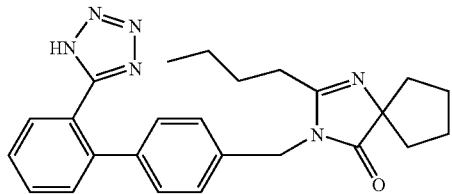

I and is described by Bernhart et al., in U.S. Pat. No. 5,270,317, which is incorporated herein by reference.

SUMMARY OF THE INVENTION

This invention is directed to various methods for preparing irbesartan and intermediates thereof as recited in the claims appended hereto.

One aspect of the present invention provides a method for preparing a compound useful in the synthesis of irbesartan, having the formula II, or a pharmaceutically acceptable salt thereof,

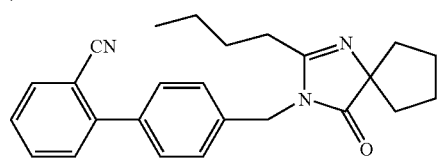

II comprising reacting a mixture of a compound of formula IVa and a compound of formula IVb, and optionally a compound of formula IVc,

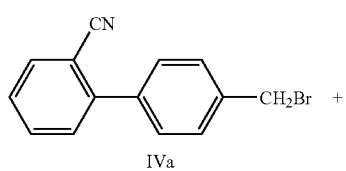

IVa

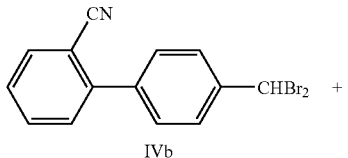

IVb

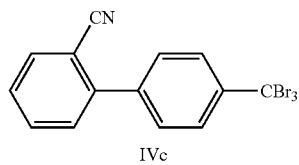

IVc with a compound of formula V, or a pharmaceutically acceptable salt thereof,

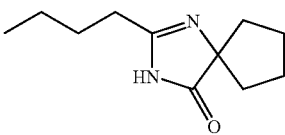

V in the presence of a base and a reducing agent, and optionally in the presence of a phase transfer catalyst; and optionally, converting the compound of formula II into a pharmaceutically acceptable salt.

Another aspect of the present invention provides a method for preparing a compound of formula I (irbesartan), or a pharmaceutically acceptable salt thereof, from the compound of formula II.

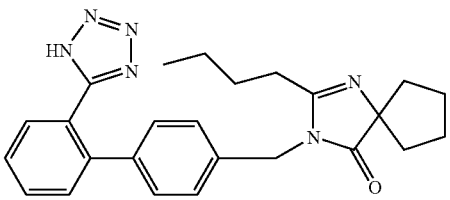

I

A further aspect of the present invention provides a method for preparing a compound of formula II in substantially pure form,

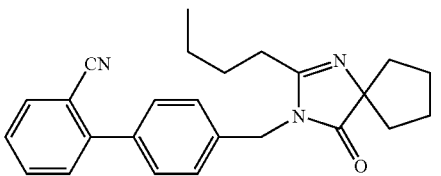

II comprising:
(a) crystallizing a crude compound of formula II with at least one solvent selected from methyl tert-butyl ether and iso-propanol to give a compound of formula II in crystal form;

(b) washing the compound of formula II in crystal form from step (a) with at least one solvent selected from methyl tert-butyl ether and iso-propanol to give the compound of formula II in substantially pure form; and
(c) recycling the washed solvent collected from step (b) to crystallize a crude compound of formula II in the next batch as recited in step (a).

DETAILED DESCRIPTION OF THE INVENTION

| ABBREVIATIONS | |
|---|---|
| HPLC: | High Pressure Liquid Chromatography |
| MTBAC: | methyl-n-tributhyl ammonium chloride |
| MTBE: | methyl tert-butyl ether |
| IPA: | isopropyl alcohol |
| NBS: | N-bromosuccinimide |

Definitions

The term "alkyl" or "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_6$ alkyl" refers to a straight or branched chain alkane (hydrocarbon) radical containing from 1 to 4 carbon atoms, such as methyl, ethyl, propyl, isopropyl, n-butyl, t-butyl, isobutyl, pentyl, isopentyl, hexyl, and isohexyl.

The term "phase transfer catalyst" refers to a small quantity of a chemical agent that enhances the rate of a reaction between chemical species located in different phases (immiscible liquids or solid and liquid) by extracting one of the reactants, most commonly an anion, across the interface into the other phase so that reaction can proceed. These catalysts include quaternary ammonium or phosphonium salts (e.g. tetraalkylammonium salts, wherein alkyl can be same or different), or agents that complex inorganic cations (e.g. crown ethers or other cryptands). The catalyst cation is not consumed in the reaction although an anion exchange does occur.

The compounds of present invention may form salts which are also within the scope of this invention. Reference to compounds of the formula I through V herein is understood to include reference to salts thereof, unless otherwise indicated. The term "salt(s)", as employed herein, denotes acidic and/or basic salts formed with inorganic and/or organic acids and bases. In addition, when a compound contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds may be formed, for example, by reacting those compounds with an amount of acid or base, such as an equivalent amount, in a medium such as one in which the salt precipitates or in an aqueous medium followed by lyophilization.

The compounds of present invention may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of present invention may also form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield compounds of the formula I through V, or a salt and/or solvate thereof. Solvates of the compounds of formula I through V include, for example, hydrates.

Compounds of the formula I through V, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Methods of Preparation

The methods for preparing compounds of formula I and II are illustrated in the following schemes. Solvents, temperatures, pressures, and other reaction conditions may readily be selected by one of ordinary skill in the art. Starting pounds IVa and IVb, and optionally IVc, can be mono-alkylated upon treatment of compound V or a pharmaceutically acceptable salt thereof, in the presence of a base, such as NaH, and in the presence of a reducing reagent, such as dialkyl phosphite (i.e., diethyl phosphite) to provide the compound of formula II. When an aqueous base such as aq. KOH or aq. NaOH is used, a phase transfer catalyst such as tetra-alkylammonium chloride is also used in addition to the reducing reagent such as dialkyl phosphite (i.e., diethyl phosphite). Here, the reducing regent selectively reduces di-brominated compound IVb (or tri-brominated compound IVc) into mono-brominated compound IVa while compound IVa is alkylated to provide the desired mono-alkylation product. This method can be applied to a mixture of compounds IVa, IVb in any ratio, i.e., the ratio between IVa:IVb can vary from 1%:99% to 99%:1%. In addition, this method also works in the presence of any amount of compound IVc. Finally, compound II can be reacted with an azide reagent, such as $NaN_3$, to give the compound of formula I.

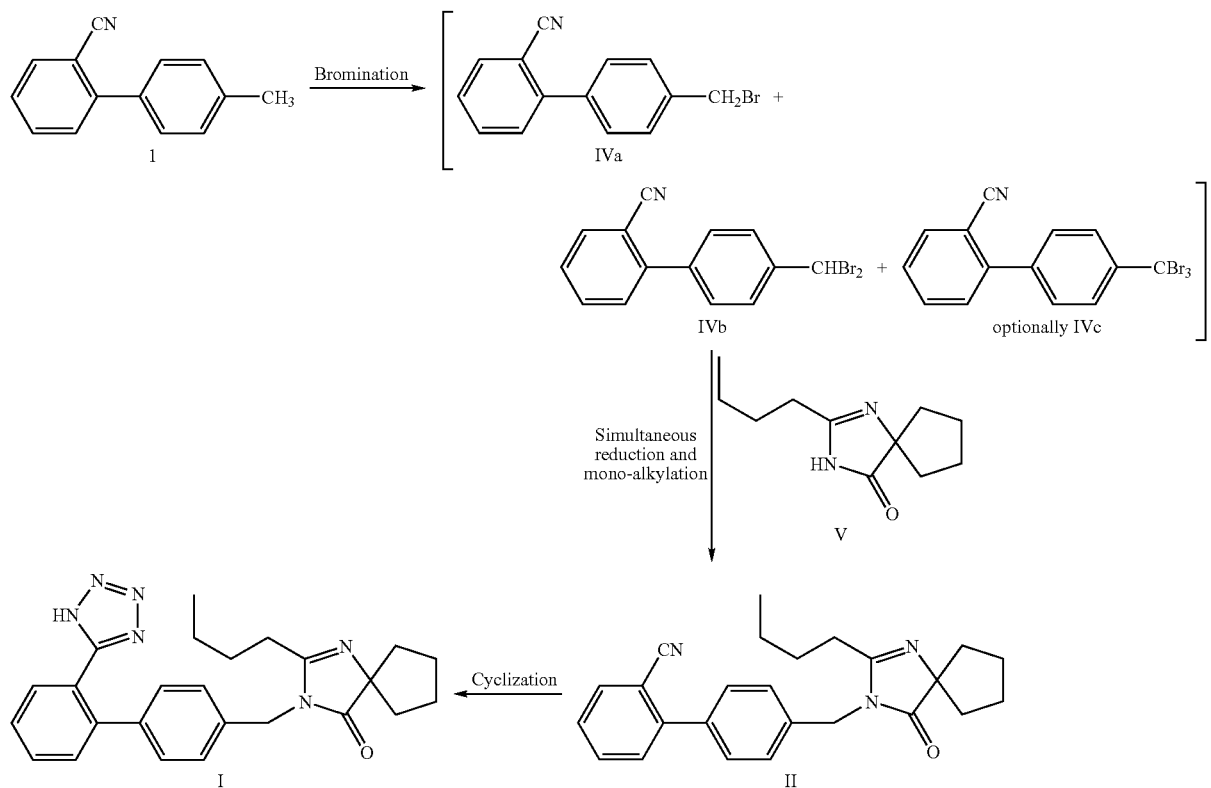

materials are commercially available or readily prepared by one of ordinary skill in the art.

The compound of formula I (irbesartan) can be prepared according to Scheme 1, Compound 1 can be brominated to give a mixture of mono-brominated product IVa and di-brominated product IVb using a brominating reagent, such as $Br_2$ or NBS, in an organic solvent, such as $CCl_4$, $CHCl_3$ or $CH_2Cl_2$, and optionally in the presence of UV light or a catalytic amount of benzoyl peroxide. A tri-brominated product IVc may also be generated if a larger excess of bromine is used. $Br_2$ can be generated in situ by reacting $NaBrO_3$ or $H_2O_2$ with HBr in water. The mixture of com- The features and advantages of the present invention are more fully shown by the following examples which are provided for purposes of illustration, and are not to be construed as limiting the invention in anyway.

EXAMPLES

HPLC Condition:
Column: Alltima C18 (Alltech 88050) 15.0 cm in length×4.6 mm in internal diameter and 5 micron particle size;

Column temperature: 40 C;
Solvent A: Buffer solution A 1.1 g of heptanesulfonic acid in 1 liter of water and adjust the pH to 2.5;
Solvent B: Methanol Flow rate: 1.2 mL/min;
Gradient Elution Condition:

| Time % | A % | % B |
| --- | --- | --- |
| 0 min | 50 | 50 |
| 35 min | 15 | 85 |

Detector: 240 nm;
Injection volume: 10 uL.

The above HPLC condition is used in the following examples unless otherwise noted.

Example 1

Preparation of Compounds of Formula IVa and IVb

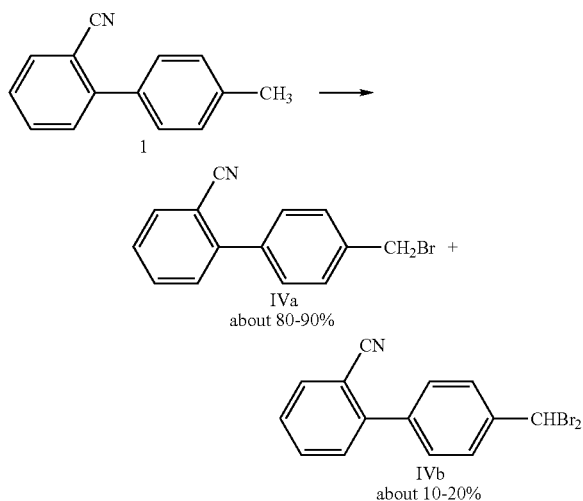

A jacketed 1,000 mL 3-neck flask was charged with 4'-methylbiphenyl-2-carbonitrile (Compound 1, 100.0 g) and $CH_2Cl_2$ (500 mL) under nitrogen. To a 500 mL Erlenmeyer flask with magnetic stirrer, sodium bromate ($NaBrO_3$; 31.2 g) was dissolved in water (170 mL). The $NaBrO_3$ solution was transferred to the 1,000 mL flask and the reaction mixture was cooled to about 5° C. or less. Aqueous HBr solution (48%, 105.0 g) was added to the 1,000 mL flask and the resulting reaction mixture was recycled though a UV lamp reactor. The reaction mixture was kept at 0-20° C. and the recycling was continued until the reaction was deemed complete by HPLC. Optionally, additional sodium bromate and hydrogen bromide may be added. The relative amounts of Compound 2 and Compound 3 were about 80-90% and about 10-20% respectively. Aqueous sodium metabisulfite solution (2.0 g of in 10 mL water) was added to the reaction mixture. Allow the phases to settle and the methylene chloride phase was washed with water and used in the next step without further purification.

Example 2

Preparation of Compound II

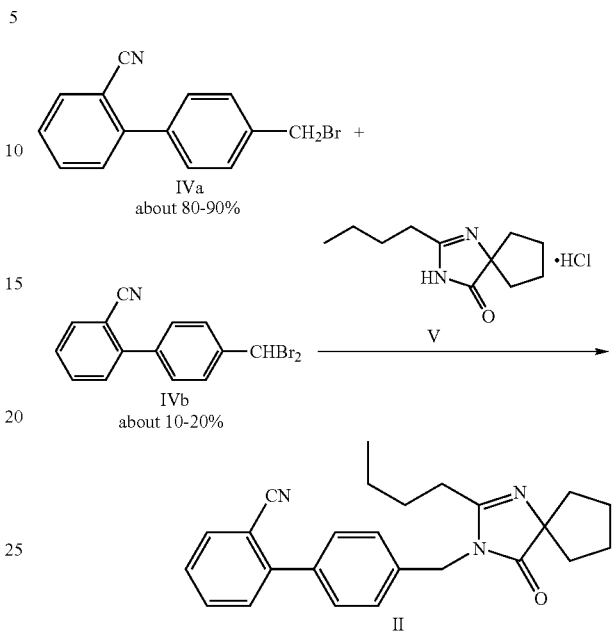

A 1 L 3-neck flask was charged with Compound V (134.0 g), MTBAC (5.0 g) and $CH_2Cl_2$ (170 mL) and cool to −5 to 5° C. An aqueous solution of KOH (182.6 g in 212 mL water) was added slowly to the 1 L flask and the reaction temperature was kept at ≦5° C. The methylene chloride solution of Compound IVa and Compound IVb from Example 1 was added to the reaction mixture slowly, while maintaining the temperature at 0-10° C. Diethyl phosphite (39.66 g) was added drop wise at 0-10° C. Check the reaction mixture for completion of the reduction reaction, and additional diethyl phosphite may be added.

The reaction mixture was allowed to warm to ambient (20-30° C.) and agitated until the reaction was deemed complete by HPLC. Water (150 mL) was added and the phases were separated. The organic layer was extracted with water (230 mL) and polish filtered.

The methylene chloride (which contained the crude Compound II) was distilled off and exchanged with about 400 mL of methyl tert-butyl ether (MTBE) (optionally, the MTBE recycled from washing below can be used here). Upon cooling, crystallization occurred (optionally seeds were added) and after further cooling to below 25° C., crystals of Compound II were isolated, washed with MTBE and dried in vacuum at a temperature of less than 60° C. HPLC retention time: 18.126 min. Typically, the yield was about 85 to about 88%. Alternatively, IPA could be used as the crystallization and washing solvent.

Optionally, the solvent (i.e., MTBE or IPA) used to wash the crystals of Compound II above can be recycled and used to crystallize the crude Compound II in the next batch. Since the washed solvent contains Compound II as well as impurities, it was surprisingly found that the washed solvent can be recovered and used again in crystallizing the crude compound of formula II in the next batch without sacrificing its purity while increasing its yield.

Example 3

Preparation of Compound I

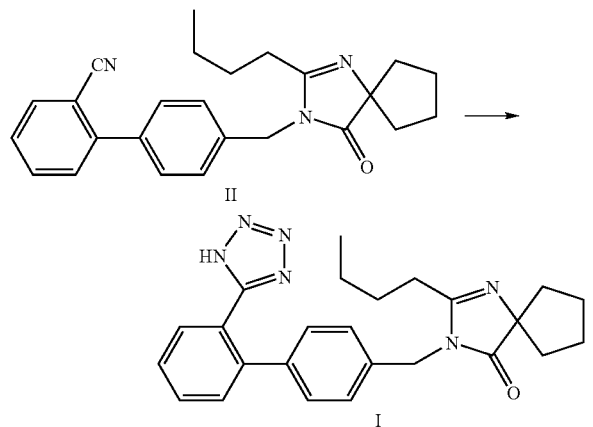

A reactor was charged with Compound II (1 kg), triethylamine chlorhydrate (0.713 kg), sodium azide (0.337 kg) and N-methyl pyrrolidinone (2.07 kg), and the reaction mixture was heated to about 122° C. under stirring. After completion of the reaction as determined by HPLC, the reaction mixture was cooled to about 45° C., and an aqueous solution of sodium hydroxide (35%, 5.99 kg) and water (3.0 kg) were added, the resulting mixture was stirred at a temperature between about 20 and about 40° C. for about 0.5 hours. The aqueous phase was discarded and the organic phase was treated with toluene (1.73 kg) and water (5.0 kg), and stirred for about 0.5 hours at about 20-about 30° C. The toluene phase was discarded and the aqueous phase was washed with ethyl acetate (1.8 kg) and treated with aqueous HCl until pH was adjusted to about 4.8-about 5.2, Precipitation occurred and the resulting suspension was stirred for about 1 hour at about 20-about 25° C. The precipitation was collected and washed with water three times (1.0 kg×3). The crude wet product was recrystallized using a mixture of iso-propanol (0.393 kg) and water (4.5 kg). HPLC retention time: 11.725 min. The yield for Compound I was about 87%.

We claim:

1. A method for preparing a compound of formula II in substantially pure form

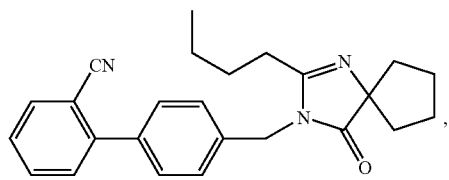

comprising reacting a mixture of a compound of formula IVa and a compound of formula IVb, and optionally a compound of formula IVc,

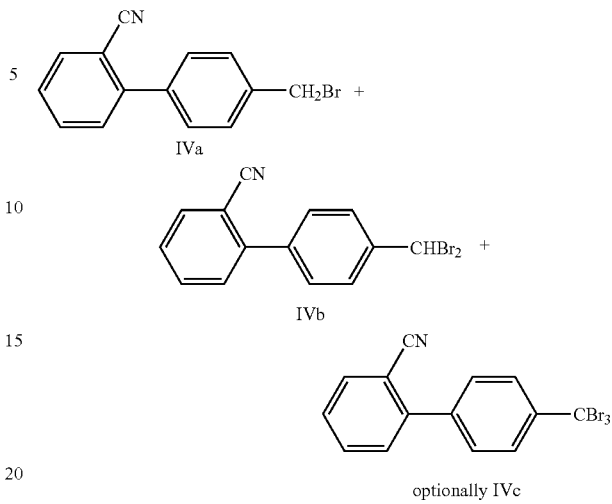

with a compound of formula V, or a pharmaceutically acceptable salt thereof,

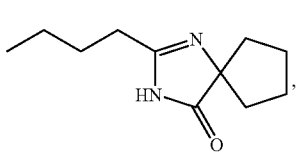

in the presence of a base and a reducing agent, and optionally in the presence of a phase transfer catalyst to form the compound of formula II, and carrying out the following steps to prepare the compound of formula II in substantially pure form:

(a) crystallizing the compound of formula II with at least one solvent selected from methyl tert-butyl ether and iso-propanol to give a compound of formula II in crystal form;

(b) washing the compound of formula II in crystal form from step (a) with at least one solvent selected from methyl tert-butyl ether and iso-propanol to give the compound of formula II in substantially pure form; and (c) recycling the washed solvent collected from step (b) to crystallize a crude compound of formula II in the next batch as recited in step (a).

2. The method of claim 1, wherein said base is aqueous KOH, aqueous NaOH, or aqueous LiOH, said phase transfer catalyst is present and is tetra-alkylammonium chloride, said reducing agent is a dialkyl phosphite, and said pharmaceutically acceptable salt of formula V is HCl.

3. The method of claim 2, wherein said tetra-alkylammonium chloride is methyl-tri-n-butyl ammonium chloride, and said dialkyl phosphite is diethyl phosphite.

4. The method of claim 1, wherein said solvent in steps (a), (b) and (c) is methyl tert-butyl ether.

5. The method of claim 1, wherein said solvent in steps (a), (b) and (c) is iso-propanol.

* * * * *